US010548938B2

(12) United States Patent
Teruya et al.

(10) Patent No.: US 10,548,938 B2
(45) Date of Patent: Feb. 4, 2020

(54) METHOD FOR MANUFACTURING COMPOSITION CONTAINING NOBILETIN AND TANGERETIN DERIVED FROM CITRUS FRUITS, AND COMPOSITION CONTAINING NOBILETIN AND TANGERETIN OBTAINED THEREBY

(71) Applicants: UNIVERSITY OF THE RYUKYUS, Nakagami-gun, Okinawa (JP); OKINAWA RESEARCH CENTER CO., LTD., Uruma-shi, Okinawa (JP)

(72) Inventors: Toshiaki Teruya, Nakagami-gun (JP); Yuto Teruya, Nakagami-gun (JP); Saki Sugiyama, Nakagami-gun (JP); Je-Tae Woo, Tokyo (JP)

(73) Assignees: UNIVERSITY OF THE RYUNKYUS, Okinawa (JP); OKINAWA RESEARCH CENTER CO., LTD., Uruma-Shi, Okinawa (JP)

( * ) Notice: Subject to any disclaimer, the term of this patent is extended or adjusted under 35 U.S.C. 154(b) by 702 days.

(21) Appl. No.: 14/435,060

(22) PCT Filed: Aug. 9, 2013

(86) PCT No.: PCT/JP2013/071664
§ 371 (c)(1),
(2) Date: Apr. 10, 2015

(87) PCT Pub. No.: WO2014/057727
PCT Pub. Date: Apr. 17, 2014

(65) Prior Publication Data
US 2015/0283196 A1    Oct. 8, 2015

(30) Foreign Application Priority Data

Oct. 12, 2012  (JP) .................. 2012-227173

(51) Int. Cl.
*A61K 36/752*    (2006.01)
*A61K 31/352*    (2006.01)

(52) U.S. Cl.
CPC .......... *A61K 36/752* (2013.01); *A61K 31/352* (2013.01)

(58) Field of Classification Search
None
See application file for complete search history.

(56) References Cited

U.S. PATENT DOCUMENTS

2002/0040052 A1* 4/2002 Ito ................... A61K 31/352
                                                    514/456
2012/0196927 A1    8/2012 Lee et al.

FOREIGN PATENT DOCUMENTS

| CN | 102603697 A    | 7/2012 |
| CN | 102875509 A    | 1/2013 |
| EP | 2 530 080 A1   | 12/2012 |
| JP | 2004-210682 A  | 7/2004 |
| JP | 2005-145824 A  | 6/2005 |
| JP | 2005-168372 A  | 6/2005 |
| JP | 2006-327998 A  | 12/2006 |
| WO | WO 2010/134373 A1 | 11/2010 |
| WO | WO 2011/092840 A1 | 8/2011 |

OTHER PUBLICATIONS

English translation of Li (CN 102603697 A)—Jul. 25, 2012.*
Database WPI Week 201355, Thomson Scientific, London, GB; AN 2013-G09258; XP002756480 (CN 102 875 509 A, Jan. 16, 2013).
Extended European Search Report dated Apr. 26, 2016, in European Patent Application No. 13845755.1.
International Search Report dated Oct. 15, 2013, in PCT International Application No. PCT/JP2013/071664.
Functional Food Materials—Arkray—Taiwan Tangerine Extract, "Use of Biletin Products," <URL: http://ebn.arkray.co.jp/products/shiikuwasha-extract/detail-02/>, (Feb. 16, 2010).
European Communication pursuant to Article 94(3) EPC, dated Aug. 14, 2017, for European Application No. 138457551.
European Patent Convention Communication for Application No. 13 845 755.1, dated Mar. 16, 2018.

* cited by examiner

*Primary Examiner* — Susan Hoffman
(74) *Attorney, Agent, or Firm* — Birch, Stewart, Kolasch & Birch, LLP

(57) ABSTRACT

The object is to provide a method of manufacturing a fraction containing nobiletin and tangeretin at high concentrations, which is excellent in terms of safety, economic efficiency, and the potential for industrialization. The method includes (1-1) a step of treating citrus fruit with hot water to obtain a hot water-treated product; (1-2) a step of drying the hot water-treated product to obtain a dried product; (1-3) a step of treating the dried product with a solvent capable of dissolving nobiletin and tangeretin to obtain a nobiletin and tangeretin solution; (3) a step of concentrating and/or drying the nobiletin and tangeretin solution to obtain a nobiletin and tangeretin concentrate; and (4) a step of treating the nobiletin and tangeretin concentrate with a dilute alkali to obtain a composition containing nobiletin and tangeretin as an insoluble component, and by a composition containing nobiletin and tangeretin at high concentrations manufactured by the method.

7 Claims, No Drawings

METHOD FOR MANUFACTURING COMPOSITION CONTAINING NOBILETIN AND TANGERETIN DERIVED FROM CITRUS FRUITS, AND COMPOSITION CONTAINING NOBILETIN AND TANGERETIN OBTAINED THEREBY

CROSS REFERENCE TO RELATED APPLICATION

The present patent application claims priority from Japanese Patent Application No. 2012-227173 filed on Oct. 12, 2012, the entire disclosure of which is incorporated herein by reference.

TECHNICAL FIELD

The present invention relates to a method of manufacturing a composition containing nobiletin and tangeretin derived from citrus fruits.

BACKGROUND ART

Nobiletin and tangeretin belong to a class of polymethoxyflavonoids that are included in citrus fruits. Nobiletin has a structure represented by the following formula (I). Tangeretin has a structure represented by the following formula (II). Nobiletin and tangeretin are said to have various pharmacological actions such as a carcinogenesis suppressing action, a blood sugar level inhibiting action, and a preventive effect for Alzheimer type dementia.

[Chem. 1]

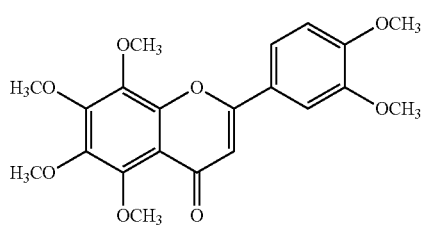

(I)

[Chem. 2]

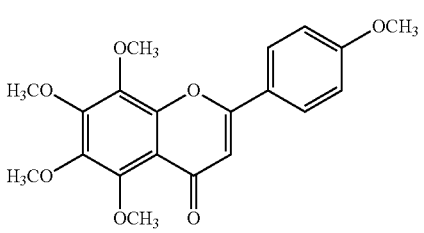

(II)

Citrus fruits such as ponkan and Taiwan tangerine are used as raw materials for the processing of juices, jams and the like in many cases. When citrus fruits are subjected to such processing, mainly the fruit pulp is utilized, and the fruit pulp left over from juice extraction or fruit peel is disposed of as juice waste. However, nobiletin and tangeretin are included in larger amounts in such juice waste than in the juice pulp. A portion of the juice waste of citrus fruit is reutilized for the extraction of essential oil or as feeds for livestock; however, the juice waste of citrus fruit is not expected as a raw material for a food product material containing nobiletin and tangeretin.

JP 2005-145824 A (hereinafter, referred to as "Patent Document 1"; the descriptions of the Patent Document 1 are incorporated herein by reference) describes a method for obtaining nobiletin by the steps of extracting thinned fruits of ponkan with 30% ethanol under reflux for 1 hour, extracting and concentrating a residue thus obtained with hot water at 90° C. or higher for 1 hour, decanting the concentrate to obtain a supernatant, passing this supernatant through a porous adsorption resin, and then eluting nobiletin with 70% ethanol.

Furthermore, JP 2006-327998 A (hereinafter, referred to as "Patent Document 2"; the descriptions of the Patent Document 2 are incorporated herein by reference) discloses a method of manufacturing polymethoxyflavonoids including nobiletin and tangeretin by the steps of obtaining a pot bottom oil by distilling the fruit peel oil of oranges under reduced pressure to remove limonene, subjecting this pot bottom oil to thin film distillation, subsequently adding about a 25-fold volume of 70% ethanol, and then heating the mixture to reflux.

Also, known as products that are currently commercially available are products sold by ARKRAY, Inc. (see Non-Patent Document 1; the descriptions of the Non-Patent Document 1 are incorporated herein by reference).

PRIOR ART DOCUMENTS

Patent Documents

Patent Document 1: JP 2005-145824 A
Patent Document 2: JP 2006-327998 A

Non-Patent Document

Non-Patent Document 1: Functional Food Materials—Arkray>>Taiwan Tangerine Extract "Use of Biletin Products"<URL: http://ebn.arkray.co.jp/products/shiiku-washa-extract/detail-02/>

SUMMARY OF THE INVENTION

Problems to be Solved by the Invention

Nobiletin, tangeretin and other polymethoxyflavonoids that are included in citrus fruits have many pharmacological actions such as described above, and therefore, the demand for these substances is ever increasing. Thus, if a method of efficiently manufacturing a naturally derived composition containing nobiletin and tangeretin (hereinafter, referred to as composition containing nobiletin and tangeretin) is available, it will be so much expected to utilize the composition containing nobiletin and tangeretin as a food material.

However, the method described in Patent Document 1 has a problem that since the method includes processes of performing extraction for one hour under reflux, and further performing extraction with hot water at 90° C. or higher, and also includes a process which uses a column. Thus, the method has problems that the operator is at high risk, and the method is economically ineffective.

The method described in Patent Document 2 includes processes for the production of a pot bottom oil by distillation under reduced pressure and the thin film distillation, and also requires a large amount of 70% ethanol. Therefore, the method has a problem of being a risky and economically inefficient method.

The product described in Non-Patent Document 1 is a product having very small percentage content of nobiletin and tangeretin because the percentage content of nobiletin and tangeretin therein is approximately 10% (w/w), and the product has a problem that the product cannot be used as a raw material for food materials.

Thus, an object of the present invention is to provide a method of manufacturing a composition containing nobiletin and tangeretin having a large percentage content of nobiletin and tangeretin, which is safe compared with the prior art technologies; and is excellent in economic efficiency and the potential for industrialization because the amount of solvent and the number of processes used in the method are quite considerable, and to provide a composition containing nobiletin and tangeretin obtainable by the method.

Means for Solving the Problems

As a result of intensive search efforts in order to achieve the object described above, the inventors of the present invention succeeded in obtaining a composition containing nobiletin and tangeretin having a high percentage content of nobiletin and tangeretin, by subjecting citrus fruit to a hot water treatment and a solvent extraction treatment, or subjecting citrus fruit to a warm solvent extraction treatment, to obtain a nobiletin and tangeretin solution, and then treating this nobiletin and tangeretin solution with a dilute alkali. Furthermore, the inventors found that such a method uses a smaller amount of solvent, can have the temperature set to a lower temperature, and comprises simple processes, as compared with the methods described in Patent Document 1 and Patent Document 2, and therefore, that the method is a method excellent in safety, economic efficiency, and the potential for industrialization. The present invention is an invention completed based on these findings.

Therefore, according to an aspect of the present invention, there is provided a method of manufacturing a composition containing nobiletin and tangeretin, comprising the following Steps (1-1) to (1-3) or Step (2), and Steps (3) and (4):

(1-1) a step of treating citrus fruit with hot water to obtain a hot water-treated product;

(1-2) a step of drying the hot water-treated product, to obtain a dried product;

(1-3) a step of treating the dried product with a solvent that is capable of dissolving nobiletin and tangeretin to obtain a nobiletin and tangeretin solution;

(2) a step of treating citrus fruit with a warm solvent that is capable of dissolving nobiletin and tangeretin, to obtain a nobiletin and tangeretin solution;

(3) a step of concentrating and/or drying the nobiletin and tangeretin solution to obtain a nobiletin and tangeretin concentrate; and (4) a step of treating the nobiletin and tangeretin concentrate with a dilute alkali, to obtain a composition containing nobiletin and tangeretin as an insoluble component.

Preferably, the method further comprises the following Step (5) as a subsequent stage of the Step (4):

(5) a step of treating the nobiletin and tangeretin concentrate by adding 10% (v/v) or less methanol to obtain a methanol-insoluble component.

Preferably, the Step (1-2) is a step of squeezing a filtration residue obtained by filtering the hot water-treated product, or drying the filtration residue without squeezing, so as to remove water from the hot water-treated product, to obtain a dried product.

Preferably, the Step (1-1) is a step of treating citrus fruit with hot water maintained at a temperature of 50° C. to 80° C. for 2 to 4 hours to obtain a hot water-treated product.

Preferably, the Step (2) is a step of treating citrus fruit for 1 to 8 hours with a warm solvent that is capable of dissolving nobiletin and tangeretin and is maintained at a temperature of 50° C. to 70° C. to obtain a nobiletin and tangeretin solution.

Preferably, the solvent that is capable of dissolving nobiletin and tangeretin, or the warm solvent that is capable of dissolving nobiletin and tangeretin is 20 to 100% (v/v) ethanol, and more preferably 20 to 50% (v/v) ethanol.

Preferably, the Step (4) is a step of treating a the nobiletin and tangeretin concentrate with a 1 to 3% (w/v) aqueous alkaline solution at room temperature to obtain a composition containing nobiletin and tangeretin as an insoluble component.

Preferably, the citrus fruit is at least one plant selected from the group consisting of *Citrus depressa, C. unshiu, C. tachibana, C. leiocarpa, C. tardiva, C. succosa, C. kinokuni, C. erythrosa, C. sunki, C. deliciosa, C. nobilis, C. reticulata, C. tangerina, C. hanayu, C. reticulata, C. sunki, C. nippokoreana*, shiranuhi, and kiyomi.

According to another aspect of the present invention, there is provided a composition containing nobiletin and tangeretin produced by the method of the present invention.

Preferably, in the composition containing nobiletin and tangeretin, the percentage content of nobiletin is 45% (w/v) or more, and the percentage content of tangeretin is 25% (w/v) or more.

Preferably, the percentage content of synephrine in the composition containing nobiletin and tangeretin is less than the lower detection limit.

According to another embodiment of the composition containing nobiletin and tangeretin of the present invention, there is provided a composition containing nobiletin and tangeretin derived from citrus fruits, wherein the percentage content of nobiletin is 45% (w/v) or more, the percentage content of tangeretin is 25% (w/v) or more, and the percentage content of synephrine is less than the lower detection limit.

According to other embodiments of the present invention, the following inventions are provided.

1. A method of manufacturing a fraction containing nobiletin and tangeretin at high concentrations, comprising a residue obtaining step of washing a juice waste obtained by squeezing fruits of a citrus fruit, with hot water, to obtain a hot water washing residue; an ethanol extract obtaining step of drying the removal residue, extracting the dry residue with 20 to 40% ethanol, to obtain an extract; a concentrate obtaining step of concentrating the ethanol extract at a low temperature, to obtain a concentrate; an alkali-insoluble component obtaining step of adding a dilute alkali to the concentrate, subsequently performing a stirring treatment, to obtain an insoluble component; and an ethanol elution step of eluting the alkali-insoluble component with ethanol.

2. The method is characterized in that the citrus fruit is selected from Taiwan tangerine (*Citrus depressa*), *C. tachibana, C. leiocarpa, C. tardiva, C. succosa, C. kinokuni, C. erythrosa, C. sunki, C. deliciosa, C. nobilis*, ponkan (*C. retuculata*), *C. tangerina, C. hanayu*, and *C. nippokoreana*.

3. The method is characterized in that the method further includes, between the concentrate obtaining step and the alkali-insoluble component obtaining step, a methanol-insoluble component obtaining step of treating the concentrate by adding methanol, and obtaining a methanol-insoluble component.

4. The method is characterized in that the heated drying in the residue obtaining step is carried out under the conditions of 50° C. to 70° C. and 15 to 45 minutes.

5. The method is characterized in that the heated drying in the residue obtaining step is carried out under the conditions of 60° C. and 30 minutes.

6. The method is characterized in that the hot water extraction in the residue obtaining step is carried out in a warm bath at 50° C. to 80° C. under the conditions of 2 to 4 hours.

7. The method is characterized in that the hot water extraction in the residue obtaining step is carried out under the conditions of 70° C. to 3 hours.

8. The method is characterized in that the acquisition of residue after the hot water extraction in the residue obtaining step is carried out using a filter having a retention particle size of 5 μm or less.

9. The method is characterized in that the heated drying in the ethanol extraction step is carried out under the conditions of 50° C. to 70° C. and 15 to 45 minutes.

10. The method is characterized in that the heated drying in the ethanol extraction step is carried out under the conditions of 60° C. and 30 minutes.

11. The method is characterized in that the ethanol extraction in the ethanol extract obtaining step is carried out at room temperature for 1 to 5 days using 20 to 40% ethanol.

12. The method is characterized in that the ethanol extraction in the ethanol extract obtaining step is carried out at room temperature using 30% ethanol.

13. The method is characterized in that the ethanol extract obtained in the ethanol extract obtaining step is concentrated for a predetermined time at a temperature of 50° C. or lower.

14. The method is characterized in that the alkali treatment in the alkali-insoluble component obtaining step is carried out for 4 to 8 days at room temperature with a 1 to 3% alkali solution.

15. The method is characterized in that the acquisition of the insoluble component in the alkali-insoluble component obtaining step is carried out using a filter having a retention particle size of 5 μm or less.

16. The method is characterized in that the insoluble component is eluted with methanol and is filtered using a filter having a retention particle size of 5 μm or less.

17. A fraction containing nobiletin and tangeretin at high concentrations, the fraction being produced by the production method described above.

18. The fraction containing nobiletin and tangeretin at high concentrations is characterized in that the content of nobiletin in the fraction is 45% (w/v), and the content of tangeretin is 25% (w/v) or more.

Advantages of the Invention

According to the method of the present invention, since the method is a method that is excellent in safety, the potential for industrialization, and economic efficiency as compared with the prior art, a citrus fruit-derived composition containing nobiletin and tangeretin at high concentrations can be produced. Furthermore, when the composition containing nobiletin and tangeretin of the present invention is used, utilization of the composition containing nobiletin and tangeretin as a food material, for example, a raw material for food and a composition for food, can be further expected. The composition containing nobiletin and tangeretin can also be supplied to applications of pharmaceutical products and cosmetic products, by utilizing the physiological activity of nobiletin and tangeretin. In that case, the composition containing nobiletin and tangeretin of the present invention can be provided in various forms such as a powder preparation, a granular preparation, a tablet preparation, a liquid preparation, a paste preparation, a capsule preparation, a gel preparation, and a cream preparation for food, cosmetic or pharmaceutical products, by the composition containing nobiletin and tangeretin itself or together with other additives.

MODES FOR CARRYING OUT THE INVENTION

Hereinafter, the present invention is described in more detail.

The method of manufacturing a composition containing nobiletin and tangeretin related to the present invention is a method characterized in that as an insoluble component, a composition containing nobiletin and tangeretin which contains nobiletin and tangeretin at high concentrations and from which components such as saccharides and fatty acids contained in citrus fruits have been removed, is produced by subjecting raw material citrus fruits to heating and solvent extraction, and subjecting a nobiletin and tangeretin solution obtained thereby to a dilute alkali treatment. The method of the present invention can be roughly divided into a first embodiment and a second embodiment, based on the difference in the processes for obtaining a nobiletin and tangeretin solution.

First, the first embodiment of the method of the present invention comprises the following Steps (1-1) to (1-3), Step (3), and Step (4):

(1-1) a step of treating citrus fruit with hot water to obtain a hot water-treated product;

(1-2) a step of drying the hot water-treated product to obtain a dried product;

(1-3) a step of treating the dried product with a solvent capable of dissolving nobiletin and tangeretin to obtain a nobiletin and tangeretin solution;

(3) a step of concentrating and/or drying the nobiletin and tangeretin solution to obtain a nobiletin and tangeretin concentrate;

(4) a step of treating the nobiletin and tangeretin concentrate with a dilute alkali to obtain a composition containing nobiletin and tangeretin as an insoluble component.

Next, the second embodiment of the method of the present invention comprises the following Step (2), Step (3), and Step (4):

(2) a step of treating citrus fruit with a warm solvent capable of dissolving nobiletin and tangeretin to obtain a nobiletin and tangeretin solution;

(3) a step of concentrating and/or drying the nobiletin and tangeretin solution to obtain a nobiletin and tangeretin concentrate;

(4) a step of treating the nobiletin and tangeretin concentrate with a dilute alkali to obtain a composition containing nobiletin and tangeretin as an insoluble component.

The citrus fruit according to the present invention is not particularly limited as long as the fruit is from a citrus plant containing nobiletin and tangeretin. Examples of the citrus fruit according to the present invention include oranges such as *Citrus chinotto*, Jaffa orange, Joppa orange, navel orange, Valencia orange, Fukuhara orange, blood orange, and bergamot; grapefruits such as orangelo and grapefruit; aroma acid citrus fruits such as kabosu, Kiyooka orange, Kaffir lime, *Citrus sulcata*, Taiwan tangerine, citron, *Citrus sudachi*, bitter orange, Niihime fruit, Buddha's hand, Yuukou mandarin, yukan fruit, yuzu, lime, and lemon; miscellaneous citrus fruits such as cocktail fruit, Amanatsu, yellow mikan, *Citrus jabara*, Shonan gold, sweetie, natsumikan, *Citrus hassaku*, Haruka, Himekoharu, and Hyuganatsu; tangors such as Akino kagayaki (dekopon), Iyokan, Ehime Kasi No. 28, kiyomi, Saga Kasi No. 34 (dekopon), shion no megumi, shiranuhi (dekopon), setoka, setomi, daimasaki (dekopon), *Citrus tankan*, harumi, hinoyutaka (dekopon), murcott, and Reikou; tangelos such as Ugli fruit, Summer fresh, Sweet spring, Seminole, tangelo, and Minneola; pomelos such as Anseikan, Kawachibankan, Banbeiyu, and pomelo (jabon); citrus fruits such as *Citrus unshiu*, Otsuyongou, Calamansi, Kanpei, *Citrus kinokuni*, *Citrus leiocarpa*, Sakurajima mikan, *Citrus tachibana*, Fujinaka mikan, ponkan, and mandarin orange; trifoliate oranges such as trifoliate orange; and kumquats such as longleaf kumquat, oval kumquat, *Fortunella crassifolia* Swingle, Jiangsu kumquat, Hong kong kumquat, and round kumquat. Preferred examples include Taiwan tangerine (*Citrus depressa*), *C. unshiu, C. tachibana, C. leiocarpa, C. tardiva, C. succosa, C. kinokuni, C. erythrosa, C. sunki, C. deliciosa, C. nobilis, ponkan* (*C. reticulata*), *C. tangerina, C. hanayu, C. reticulata, C. sunki, C. nippokoreana*, shiranuhi, and kiyomi. The citrus fruit according to the present invention may be of one kind or two or more kinds, and may also be a hybrid of the citrus fruits listed above as preferred examples.

The parts of citrus fruit that can be utilized in the present invention are not particularly limited as long as the parts are parts containing nobiletin and tangeretin; however, for example, fruit peel, juice waste (pomace), pruned leaves and twigs, and dried products thereof can also be used as raw materials, in addition to fruit. In the case of Taiwan tangerine and ponkan, it is preferable to use fruit, fruit peel, and juice waste, since these parts have high contents per unit weight of nobiletin and tangeretin. On the other hand, pruned leaves and twigs do not have contents of nobiletin and tangeretin per unit weight that are comparable to those in fruit peel; however, pruned leaves and twigs are produced in large quantities. For this reason, there is a possibility that the burden on the environment may be reduced by using these.

The method for obtaining juice waste of citrus fruit is not particularly limited; however, juice waste can be obtained by treating the fruits of a citrus fruit with a squeezing machine. The squeezing machine is not particularly limited; however, it is preferable to use a roll pressing machine, a filter cloth pressing machine, a centrifugal filtration type separation apparatus, or the like, because juiced fruit peel can be efficiently obtained.

The method for obtaining a dried product of fruit, fruit peel, and juice waste of citrus fruit is not particularly limited; however, for example, a dried product of citrus fruit can be obtained by heating and drying citrus fruit under the conditions of 50° C. to 70° C. for 15 to 45 minutes. In this case, if the fruit is dried at a temperature below 50° C., there is a possibility that the fruit may not be sufficiently dried in a short time such as 15 to 45 minutes, and if the fruit is dried at a temperature higher than 70° C., there is a possibility that the components contained in the citrus fruit may be degenerated during drying. Thus, when citrus fruit is dried under heating, it is preferable to dry the fruit at about 60° C. for about 30 minutes.

In Step (1-1), a hot water-treated product is obtained by treating citrus fruit with hot water. When citrus fruit is treated with hot water, saccharides can be removed by eluting the saccharides in the citrus fruit into hot water, or the like. The hot water is preferably hot water that is maintained at a temperature of 50° C. or higher. If the temperature of the hot water is lower than 50° C., there is a possibility that water-soluble contaminants in the citrus fruit may not be sufficiently eliminated. On the other hand, if the temperature of the hot water is higher than 80° C., there is a risk for the process operator, and fuel costs are also required. Therefore, the temperature of the hot water is more preferably 50° C. to 80° C. The time for treating the citrus fruit with hot water is not particularly limited as long as the time is a time period in which water-soluble contaminants in the citrus fruit can be sufficiently eliminated; however, for example, the time is 1 hour or longer, preferably 2 hours or longer, and more preferably 2 to 4 hours. A preferred embodiment of Step (1-1) is a step of obtaining a hot water-treated product by treating, for example, citrus fruit with hot water that is maintained at a temperature of 50° C. to 80° C. for 2 to 4 hours. There are no particular limitations on the specific embodiment of Step (1-1); however, for example, a step of introducing a container containing citrus fruits in distilled water, into a warm bath, and maintaining the container at a temperature of 50° C. to 80° C. for 2 to 4 hours, may be included. Here, it is more preferable to perform the hot water treatment under the conditions of about 70° C. for about 3 hours.

The hot water-treated product obtained in Step (1-1) is a mixture of citrus fruits and water. Thus, from the viewpoints of the drying efficiency or acquisition efficiency for the subsequent stage, Step (1-2), it is preferable to obtain the hot water-treated product as a solid residue by means of a conventionally known solid-liquid separation technique, such as filtration treating the hot water-treated product using a filter having a retention particle size of 5 μm or less. When a filter is used, the efficiency can be further increased if the retention particle size is set to 3 μm or less. Furthermore, when the citrus fruit used in Step (1-1) is fruit or fruit peel, it is preferable to provide juice waste by squeezing the hot water-treated product or a residue of the hot water-treated product, from the viewpoint of the drying efficiency or acquisition efficiency of the subsequent stage, Step (1-2). Thus, in regard to the method of the present invention, a step of obtaining a residue of the hot water-treated product, or a step of squeezing a residue of the hot water-treated product to obtain juice waste can be provided as a subsequent stage of Step (1-1). Meanwhile, according to the present invention, the hot water-treated product incorporates a product that is processed so as to reduce water from the hot water-treated product, such as a residue of the hot water-treated product and juice waste, in addition to the hot water-treated product obtained in Step (1-1).

In Step (1-2), a dried product is obtained by drying the hot water-treated product obtained in Step (1-1). This drying is not particularly limited as long as the hot water-treated product is dried to the extent that the percentage water content is less than several ten percent (%), and preferably less than 10%. However, it is preferable that the drying involves heated drying carried out under the conditions of about 50° C. to 80° C. and several ten minutes to several ten hours. If the hot water-treated product is dried at a temperature lower than 50° C., there is a possibility that sufficient drying may not be achieved in a short time such as several ten minutes. On the other hand, if the hot water-treated product is dried at a temperature higher than 80° C., there is a possibility that the components contained in the hot water-treated product may be degenerated during drying. Thus, on the occasion of industrialization, the hot water-treated product is preferably dried using a dryer or the like, at about 50° C. to 80° C. for several hours to several ten hours, and more preferably at about 70° C. for 12 to 24 hours. When such a drying treatment is carried out, a dried product containing nobiletin and tangeretin and having a percentage water content of less than about 10% is obtained through Step (1-2).

In Step (1-3), the dried product obtained in Step (1-2) is treated with a solvent capable of dissolving nobiletin and tangeretin, and thereby a nobiletin and tangeretin solution is obtained. The solvent capable of dissolving nobiletin and tangeretin is not particularly limited as long as it is a solvent which can dissolve nobiletin and tangeretin, and examples thereof include solvents which can easily dissolve nobiletin and tangeretin, while specific examples include organic solvents such as ethanol and ethyl acetate; and mixed solvents of these organic solvents and water. In the case of using a mixed solvent of ethanol and water as the solvent capable of dissolving nobiletin and tangeretin, for example, 20 to 100% (v/v) ethanol can be used. However, if the ethanol concentration is less than 20% (v/v), there is a possibility that the extraction efficiency may be poor, and even if the ethanol concentration is more than 50% (v/v), the extraction efficiency is not much increased. Accordingly, 20 to 50% (v/v) ethanol is preferable as the solvent capable of dissolving nobiletin and tangeretin, and 30% (v/v) ethanol is more preferable from the viewpoints of the extraction efficiency, safety, and the potential for industrialization. Furthermore, the treatment conditions for Step (1-3) are not particularly limited as long as the conditions are conditions suitable for nobiletin and tangeretin in the dried product to dissolve in the solvent, and the conditions may be determined by appropriately performing sampling and checking the concentrations of nobiletin and tangeretin in the solution. However, for example, the treatment can be carried out under the conditions of 1 to 5 days at room temperature, and it is preferable to perform the treatment for 3 days at room temperature from the viewpoint of extraction efficiency. The recovery ratio of nobiletin and tangeretin in the nobiletin and tangeretin solution is not particularly limited; however, the recovery ratio of nobiletin and tangeretin based on the presumed content of nobiletin and tangeretin (59 mg/g) contained in the raw material citrus fruit, is preferably 40% (23.6 mg/g) or more, more preferably 70% (41.3 mg/g) or more, even more preferably 90% (53.1 mg/g) or more, and still more preferably 95% (56.1 mg/g) or more.

The nobiletin and tangeretin solution obtainable by Step (1-3) comprises a certain amount of solid components. Thus, from the viewpoint of the treatment efficiency of the subsequent stage, Step (4), it is preferable to subject the nobiletin and tangeretin solution obtained by Step (1-3) to a solid-liquid separation technique such as filtration using a filter having a retention particle size of 10 μm or less, and preferably a filter having a retention particle size of 3 μm or less, and to obtain the solution as a liquid component. Thus, according to the present invention, the nobiletin and tangeretin solution incorporates a solid-containing nobiletin and tangeretin solution obtainable by Step (1-3) as well as a liquid nobiletin and tangeretin solution having solid components removed therefrom.

In Step (2), a nobiletin and tangeretin solution is obtained by treating citrus fruit with a warm solvent capable of dissolving nobiletin and tangeretin. In Step (2), in order to efficiently elute nobiletin and tangeretin in the citrus fruit by means of a warm solvent capable of dissolving nobiletin and tangeretin, the citrus fruit used in Step (2) is preferably in the form of juice waste or a dried product of juice waste. The warm solvent capable of dissolving nobiletin and tangeretin is a solvent capable of dissolving nobiletin and tangeretin that is maintained at 50° C. to 70° C., and preferably at about 60° C. The treatment time for Step (2) is not particularly limited as long as the time is a time period in which nobiletin and tangeretin in citrus fruit can be sufficiently eluted into the solvent; however, for example, the treatment time is 1 hour or longer, preferably 2 hours or longer, and more preferably 4 to 8 hours. The nobiletin and tangeretin solution obtainable by the solvent treatment of Step (2) is preferably obtained as a liquid component, by subjecting the nobiletin and tangeretin solution to a solid-liquid separation technique such as filtration using a cartridge filter having a retention particle size of 10 μm, similarly to Step (1-3).

The method of the present invention comprises Step (3) of concentrating, drying or concentrating and drying the nobiletin and tangeretin solution obtained in Step (1-3) or Step (2) to obtain a nobiletin and tangeretin concentrate. The method for concentrating the nobiletin and tangeretin solution is not particularly limited; however, for example, a method of volatilizing the solvent in the nobiletin and tangeretin solution at a low temperature over a predetermined time to obtain a concentrate containing nobiletin and tangeretin in the form of a solid dry state, may be included. Concentration of nobiletin and tangeretin is not particularly limited as long as a concentrate of nobiletin and tangeretin having a reduced volume can be obtained by removing the solvent capable of dissolving nobiletin and tangeretin. However, for example, in a case in which 20 to 100% (v/v) ethanol is used as the solvent capable of dissolving nobiletin and tangeretin, concentration is carried out at a temperature of 50° C. or lower for several ten minutes to several hours, and preferably for 10 minutes to 2 hours, in consideration of the prevention of degeneration of the contained components. Furthermore, the method for drying the nobiletin and tangeretin solution is not particularly limited; however, for example, a method of heating and drying, or freezing and drying, the nobiletin and tangeretin solution or a concentrate thereof may be included.

In Step (4), the nobiletin and tangeretin concentrate is treated with a dilute alkali, and thereby a composition containing nobiletin and tangeretin is obtained as an insoluble component. When the nobiletin and tangeretin concentrate is treated with a dilute alkali, contaminant components such as fatty acids in the solution are removed, and a composition containing nobiletin and tangeretin at high concentrations can be obtained. The dilute alkali is not particularly limited as long as it degrades contaminants in the nobiletin and tangeretin concentrate, but does not degrade nobiletin and tangeretin, and an example thereof may be an aqueous solution of a dilute alkali selected from the group consisting of an aqueous solution of sodium hydroxide and an aqueous solution of potassium hydroxide. The alkali concentration of the dilute alkali is not particularly limited, but for example, when the dilute alkali is an aqueous solution of sodium hydroxide, the alkali concentration can be adjusted to 0.1% to 20% (w/v), preferably 0.5% to 10% (w/v), and more preferably 1% to 3% (w/v).

The dilute alkali treatment of the nobiletin and tangeretin concentrate in Step (4) can be carried out, for example, for 1 to 6 days at room temperature by bringing the nobiletin and tangeretin concentrate into contact with a 1 to 3% (w/v) alkali solution. There are no particular limitations on the specific embodiment of Step (4); however, the dilute alkali treatment can be carried out by stirring a mixture of the nobiletin and tangeretin concentrate and a 1% (w/v) aqueous solution of sodium hydroxide for 1 to 2 days at room temperature.

As a result of performing Step (4), a composition containing nobiletin and tangeretin is obtained as an insoluble component. In order to collect the composition containing nobiletin and tangeretin, conventionally known solid-liquid separation techniques such as centrifugation and filtration can be used. Furthermore, in a case in which the composition containing nobiletin and tangeretin is used as, for example, a food raw material, it is preferable to neutralize the material by washing with water, or the like. Furthermore, the composition containing nobiletin and tangeretin can be supplied to a purification process. For example, a composition containing nobiletin and tangeretin having reduced impurities can be obtained as a liquid component, by subjecting a mixture of a composition containing nobiletin and tangeretin that has been collected and washed with water, and a solvent capable of dissolving nobiletin and tangeretin, to solid-liquid separation.

The composition containing nobiletin and tangeretin obtainable according to the method of the present invention is a citrus fruit-derived composition containing nobiletin and tangeretin at higher concentrations as compared with the prior art technologies; however, for example, the composition containing nobiletin and tangeretin is preferably a composition containing nobiletin and tangeretin having a percentage content of nobiletin and tangeretin of 25% (w/v) or more, and is more preferably a composition containing nobiletin and tangeretin having a percentage content of nobiletin of 45% (w/v) or more and a percentage content of tangeretin of 25% (w/v) or more.

Furthermore, the inventors of the present invention found that the composition containing nobiletin and tangeretin obtainable according to the method of the present invention has a very small percentage content of synephrine, which has a possibility of adversely affecting the human body. Thus, a preferred embodiment of the method of the present invention is a method of manufacturing a composition containing nobiletin and tangeretin having a percentage content of synephrine of less than 0.5% (w/v), and preferably having a percentage content of synephrine of less than the lower detection limit. The contents of nobiletin, tangeretin and synephrine can be measured by the method described in Examples described below.

The method of the present invention may also comprise various processes in addition to the processes described above, as long as the object of the present invention can be achieved. For example, the method may include steps of mixing the nobiletin and tangeretin concentrate with an organic solvent which does not dissolve nobiletin and tangeretin, and obtaining an insoluble component by a solid-liquid separation technique, as a previous stage of Step (4). Furthermore, after the relevant step, a step of mixing this insoluble component with a solvent capable of dissolving nobiletin and tangeretin, and then obtaining a soluble component by a solid-liquid separation technique, or a step of concentrating this soluble component may be added. The organic solvent that does not dissolve nobiletin and tangeretin is not particularly limited; however, examples thereof include methanol and ethanol at 10% (v/v) or less.

As another embodiment, the method of the present invention can also be expressed as a method of manufacturing a fraction containing nobiletin and tangeretin at high concentrations, comprising a residue obtaining step of squeezing and drying the fruits of a citrus fruit, or washing the fruits of a citrus fruit with hot water without squeezing and drying, to obtain a hot water washing residue; an ethanol extract obtaining step of drying the removed residue, extracting the residue with 20 to 40% ethanol, to obtain an extract; a concentrate obtaining step of concentrating the ethanol extract at a low temperature, to obtain a concentrate; an alkali-insoluble component obtaining step of adding a dilute alkali to the concentrate, subsequently performing a stirring treatment, and obtaining an insoluble component; and an ethanol elution step of eluting the alkali-insoluble component with ethanol.

The composition containing nobiletin and tangeretin manufactured by the method of the present invention may be incorporated in the present invention as different embodiments. The composition containing nobiletin and tangeretin of the present invention is not particularly limited as long as it is a citrus fruit-derived composition which is manufactured by the method of the present invention and contains nobiletin and tangeretin at high concentrations compared with the prior art; however, for example, from the viewpoint of the cost required when obtained products are produced by applying the composition containing nobiletin and tangeretin as a food raw material, a composition containing nobiletin and tangeretin having percentage contents of nobiletin and tangeretin of 25% (w/v) or more is preferred, and a composition containing nobiletin and tangeretin having a percentage content of nobiletin of 45% (w/v) or more and a percentage content of tangeretin of 25% (w/v) or more is more preferred. Furthermore, the composition containing nobiletin and tangeretin of the present invention is more preferably a composition having a percentage content of synephrine of less than 0.5% (w/v), and even more preferably a composition having a percentage content of synephrine of less than the lower detection limit. Furthermore, as another embodiment of the composition containing nobiletin and tangeretin of the present invention, there is provided a citrus fruit-derived composition containing nobiletin and tangeretin having a percentage content of nobiletin of 45% (w/v) or more, a percentage content of tangeretin of 25% (w/v) or more, and a percentage content of synephrine of less than the lower detection limit.

As a specific embodiment of the method of the present invention, a method of manufacturing a fraction containing nobiletin and tangeretin at high concentrations using a juice waste pomace obtained by squeezing Taiwan tangerine as a raw material, is described below, but the method of the present invention is not intended to be limited to the following embodiment.

First, Taiwan tangerine is washed with water, and subsequently, a squeezing treatment is carried out using various squeezing machines that can directly squeeze the fruits of Taiwan tangerine. Examples of such a squeezing machine include a roll press juicer in which two compressing rolls having a 10- to 20-mesh endless net interposed therebetween are caused to rotate, and the fruits of Taiwan tangerine continuously supplied to the machine are squeezed with these two compressing rolls; a filter cloth pressing machine in which the fruits of Taiwan tangerine are wrapped by a filter cloth, and are compressed and juiced; and a centrifugal filtration type separation apparatus.

A predetermined amount, for example, about 300 g to about 500 g (wet weight), of juice waste obtained by squeezing juice is weighed. Subsequently, this residue is dried using a dryer or the like, for example, at about 50° C. to about 70° C. The weight of the dried juice waste (dry weight) is weighed, and then the dry juice waste is introduced into an appropriate container. Distilled water in an amount of 1 to 2 times the dry weight is added to the container, this container is transferred into a warm bath at about 60° C. to about 80° C., and extraction is carried out for 1 to 3 hours. After the extraction, the beaker is taken out from the warm bath and naturally cooled. Subsequently, for example, a filter paper having a retention particle size of 5 µm or less is spread in a Buchner funnel, the entire amount of the extract is subjected to suction filtration, and the residue is separated by filtration.

The residue thus obtained is dried again in the same manner as described above, at about 50° C. to about 70° C. using a dryer or the like, and the residue is weighed. Ethanol in an amount of 2 to 3 times the dry weight is added thereto, and extraction is carried out for 2 to 4 days at room temperature. Subsequently, the entire amount of the extract is subjected to suction filtration as described above, and the residue is separated by filtration. The filtrate is concentrated at about 30° C. to 40° C. for about 15 minutes to about 60 minutes.

To the concentrate thus obtained, a 1% (w/v) aqueous solution of sodium hydroxide in an amount of 8 to 10 times the volume of this concentrate is added, and the mixture is thoroughly mixed at room temperature. This mixed liquid is continuously stirred for 1 to 2 days at room temperature using, for example, a stirrer. Thereafter, for example, a filter paper having a retention particle size of 5 µm or less is mounted on a funnel, and the mixed liquid is naturally filtered to separate a soluble component and an insoluble component. The insoluble component thus obtained is washed with a 1- to 2-fold amount of water. The residual insoluble component is eluted with a 5- to 10-fold amount of ethanol. Thereafter, the ethanol-soluble portion is concentrated for about 15 minutes to about 60 minutes at room temperature. The amount of liquid after concentration is reduced to about 1/15 to 1/20 of the weight before concentration, and this amount of liquid is measured.

To this concentrate, an approximately 0.5 to 2% (w/v) aqueous solution of sodium hydroxide in an amount of 8 to 10 times the amount of liquid is added, and the mixture is thoroughly mixed. Subsequently, this mixed liquid is continuously stirred for 4 to 8 days at room temperature using, for example, a stirrer. Thereafter, for example, a filter paper having a retention particle size of 5 µm or less is mounted on a funnel, the mixed liquid is naturally filtered, and the residue is separated by filtration. In this manner, a fraction containing nobiletin and tangeretin at high percentage contents can be obtained.

Hereinafter, the present invention will be described in more detail by way of Examples. However, the present invention is not intended to be limited to the following Examples.

EXAMPLES

The contents (mg) of nobiletin and tangeretin were measured by a calibration curve method using a Develosil ODS-HG-5 column as a column and MeOH:H$_2$O=70:30 as a mobile phase under the conditions set at a flow rate of 1 ml/min and a measurement wavelength of 215.0 nm, by defining the compounds as peaks having retention times of about 8 to 9 minutes and about 11 to 12 minutes, respectively.

The content (mg) of synephrine was measured by a calibration curve method using a Develosil ODS-HG-5 column as a column and CH$_3$CN:H$_2$O=2:98 (containing 0.1% TFA) as a mobile phase under the conditions set at a flow rate of 1 ml/min and a measurement wavelength of 223.0 nm, by defining the compound as a peak having a retention time of about 8 to 9 minutes, respectively.

Example 1

500 g of a pomace of Taiwan tangerine produced from Higashimura in Okinawa Prefecture was thoroughly washed, 1800 mL of distilled water at about 70° C. was added thereto, and the mixture was heat treated by placing the mixture in a water bath at about 70° C. for 3 hours. The heat treated product thus obtained was subjected to suction filtration using a Buchner funnel with a filter paper (manufactured by Advantec MFS, Inc., No. 131) having a retention particle size of 3 µm spread thereon, and thus a residue was obtained. The residue was subjected to a squeezing machine and was juiced.

300 g (wet weight) of the juice waste obtained after juicing was weighed, and the juice waste was dried for 30 minutes at about 60° C. using a dryer (manufactured by Panasonic Corp., product No. EH5101P TurboDry). Thus, 150 g of dried fruit peel was obtained. 30% (v/v) Ethanol in an amount of 2 times the weight of the juice waste was added thereto, and ethanol extraction was carried out for 3 days at room temperature. The extract was subjected to suction filtration using a Buchner funnel provided with a filter paper (manufactured by Advantec MFS, Inc., No. 131) having a retention particle size of 3 µm spread thereon, and thus 3200 mg of a filtrate was obtained ("After ethanol extraction (1)" in Table 1). The filtrate thus obtained was concentrated in a rotary evaporator, and thus a concentrate was obtained.

A 10-fold amount of a 1% (w/v) aqueous solution of sodium hydroxide was added to the concentrate, and the mixture was stirred for 1 day at room temperature using a stirrer. An insoluble component thus obtained was washed with a double amount of water. The residual insoluble component was eluted with a 5- to 10-fold amount of 100% (v/v) ethanol. Subsequently, the ethanol-eluted component was treated to separate a precipitate by filtration using a Buchner funnel. The contents of nobiletin and tangeretin in 66.3 mg of a solid-dried concentrate of the filtrate thus obtained were measured by HPLC, and as indicated in Table 1, the contents were 34.0 mg and 16.8 mg, respectively, while the percentage content was about 77% by weight. Meanwhile, the recovery ratio (%) was determined by assuming the contents of nobiletin and tangeretin included in 500 g of the pomace of Taiwan tangerine as 500 mg.

TABLE 1

| | Component | | | | |
| --- | --- | --- | --- | --- | --- |
| | Nobiletin | | Tangeretin | | |
| Step | Content (mg) | Percentage content (wt %) | Content (mg) | Percentage content (wt %) | Recovery ratio (%) |
| After ethanol extraction (1) | 70.4 | 2.2 | 32.0 | 1.0 | 20.4 |
| After ethanol elution after alkali treatment (2) | 34.0 | 51.3 | 16.8 | 25.4 | 10.1 |

Example 2

500 g of a pomace of Taiwan tangerine produced from Higashimura in Okinawa Prefecture was thoroughly washed, 1800 mL of distilled water at about 70° C. was added thereto, and the mixture was heat treated by placing the mixture in a water bath at about 70° C. for 3 hours. The heat treated product thus obtained was subjected to suction filtration using a Buchner funnel with a filter paper (manufactured by Advantec MFS, Inc., No. 131) having a retention particle size of 3 µm spread thereon, and thus a residue was obtained.

500 g (wet weight) of the residue was weighed, and the residue was dried for 30 minutes at about 60° C. using a dryer (manufactured by Panasonic Corp., product No. EH5101P TurboDry). Thus, 225 g of dried fruit peel was obtained. 100% (v/v) Ethanol in an amount of 2 times the weight of the juice waste was added thereto, and ethanol extraction was carried out for 3 days at room temperature. The extract was subjected to suction filtration using a Buchner funnel provided with a filter paper (manufactured by Advantec MFS, Inc., No. 131) having a retention particle size of 3 μm spread thereon, and thus a filtrate was obtained. The filtrate was concentrated and solid-dried, and 13.1 g of a concentrated solid-dried product was obtained ("After ethanol extraction (1)" in Table 2). The filtrate thus obtained was concentrated with a rotary evaporator, and thus a concentrate was obtained.

A 10-fold amount of a 1% (w/v) aqueous solution of sodium hydroxide was added to the concentrate, and the mixture was stirred for 1 day at room temperature using a stirrer. An insoluble component thus obtained was washed with a double amount of water. The residual insoluble component was eluted with a 5- to 10-fold amount of 100% (v/v) ethanol. Subsequently, the ethanol-eluted component was treated to separate a precipitate by filtration using a Buchner funnel. The contents of nobiletin and tangeretin in 76.0 mg of a composition containing nobiletin and tangeretin obtained by concentrating and solid-drying the filtrate were measured by HPLC, and as indicated in Table 2, the contents were 43.9 mg and 26.8 mg, respectively, while the percentage content was about 93% by weight. In the following Table 2, the contents, percentage contents and recovery ratios of nobiletin and tangeretin were determined in the same manner as in Example 1 described above.

TABLE 2

| | Component | | | | |
| --- | --- | --- | --- | --- | --- |
| | Nobiletin | | Tangeretin | | |
| Step | Content (mg) | Percentage content (wt %) | Content (mg) | Percentage content (wt %) | Recovery ratio (%) |
| After ethanol extraction (1) | 368 | 2.8 | 172 | 1.3 | 108 |
| After ethanol elution after alkali treatment (2) | 43.9 | 57.8 | 26.8 | 35.3 | 14.1 |

Example 3

50 g (wet weight) of a pomace of Taiwan tangerine was weighed, and the pomace was dried for 30 minutes at about 60° C. using a dryer (manufactured by Panasonic Corp., product No. EH5101P TurboDry). Thus, 15 g of dried fruit peel was obtained. 100 mL of distilled water at about 70° C. was added to the dried fruit peel thus obtained, the mixture was placed in a water bath at about 70° C., and heating and extraction was carried out for 3 hours. An extract thus obtained was subjected to suction filtration using a Buchner funnel provided with a filter paper (manufactured by Advantec MFS, Inc., No. 131) having a retention particle size of 3 μm spread thereon, and thus a residue was obtained.

The residue thus obtained was dried, 100% (v/v) ethanol in an amount of 2 times the weight of the juice waste was added thereto, and ethanol extraction was carried out for 3 days at room temperature. The extract was subjected to suction filtration using a Buchner funnel provided with a filter paper (manufactured by Advantec MFS, Inc., No. 131) having a retention particle size of 3 μm spread thereon, and thus a filtrate was obtained ("After ethanol extraction (1)" in Table 3). The filtrate thus obtained was concentrated with a rotary evaporator, and thus 1.15 g of a concentrate in a solid-dry state was obtained. 10% (v/v) Methanol in an amount of 2 times the weight of the concentrate thus obtained was added to the concentrate, the concentrate was dissolved therein, and solution was centrifuged at 4×15 g for 30 minutes at room temperature. Thus, the concentrate was separated into a 10% methanol-insoluble component and a soluble component.

50% (v/v) Ethanol in a one-fold amount was added to the 10% (v/v) methanol-insoluble component thus obtained, and the mixture was centrifuged at 4×10 g for 30 minutes at room temperature. Furthermore, the mixture was divided into an insoluble component and a soluble component. The soluble component was concentrated for 30 minutes at 40° C., a 1% (w/v) aqueous solution of sodium hydroxide in a 10-fold amount was added thereto, and the mixture was stirred for 6 days at room temperature using a stirrer. Subsequently, the mixture was subjected to suction filtration using a Buchner funnel provided with a filter paper (manufactured by Advantec MFS, Inc., No. 131) having a retention particle size of 3 μm spread thereon, and thus a precipitate and a filtrate were separated by filtration. The precipitate thus obtained was washed with a double amount of water, and subsequently, the precipitate was eluted with a 5- to 10-fold amount of 100% (v/v) ethanol. Subsequently, the ethanol-eluted component was treated to separate a precipitate by filtration using a Buchner funnel. The filtrate thus obtained was concentrated and solid-dried, and thus 28.4 mg of a purification product containing nobiletin and tangeretin at high concentrations was obtained. The contents of nobiletin and tangeretin in the purification product were measured by HPLC, and as indicated in Table 3, the contents were 14.1 mg and 11.2 mg, respectively, while the percentage content was about 89% by weight. In the following Table 3, the contents, percentage contents and recovery ratios of nobiletin and tangeretin were determined in the same manner as in Example 1 described above.

TABLE 3

| | Component | | | | |
| --- | --- | --- | --- | --- | --- |
| | Nobiletin | | Tangeretin | | |
| Step | Content (mg) | Percentage content (wt %) | Content (mg) | Percentage content (wt %) | Recovery ratio (%) |
| After ethanol extraction (1) | 32.2 | 2.8 | 17.2 | 1.5 | 98.8 |
| After ethanol elution after alkali treatment (2) | 14.1 | 49.7 | 11.2 | 39.4 | 50.6 |

As described above, fractions containing nobiletin and tangeretin at high concentrations were obtained. Since the fractions thus obtained contain nobiletin and tangeretin at concentrations several times higher than those of fractions that have been produced hitherto, these compounds can be conveniently produced. Furthermore, when the high-concentration fractions obtained according to the method of the present invention are used, superiority is increased in view of cost on the occasion of producing these compounds and analogues thereof.

Example 4

Powders containing nobiletin and tangeretin at high concentrations of Lots 1 to 3 described below were obtained.

[Lot 1]

70 kg of a dried pomace of Taiwan tangerine was subjected to extraction for 2 hours at 60° C. using 450 L of 30% (v/v) ethanol. Extracts after the passage of 1 hour and 2 hours from the extraction, and the extract concentrated thereafter were sampled, and then the samples were filtered through cartridge filters (retention particle size: 10 μm). Subsequently, the filtrates were concentrated, and thus the amount of the solution was decreased to 130 L. A 2% (w/v) aqueous solution of sodium hydroxide in the same amount as the amount of the solution (130 L) was added thereto, and the solution was stirred overnight at room temperature. Thereafter, the solution was centrifuged, and 319 g (wet weight) of a precipitate powder was obtained. An operation of immersing the powder thus obtained in water and then filtering the powder was repeated twice. The powder was washed with water and filtered again, and then the residue on the filter paper was immersed in ethanol. The residue was suction filtered, and an ethanol extract thus obtained was concentrated. Thus, 62.5 g of a high nobiletin- and tangeretin-containing powder (percentage content of nobiletin: 42.8 wt %, and percentage content of tangeretin: 45.9 wt %) was obtained. The results are presented in Table 4.

[Lot 3]

55 kg of a dried pomace of Taiwan tangerine was subjected to extraction for 1 hour at 60° C. using 450 L of 30% (v/v) ethanol. The extract was left to stand overnight at room temperature, and then was filtered through a cartridge filter (retention particle size: 10 μm). Subsequently, the filtrate was concentrated, and the amount of the solution was decreased to 95 L. 5 L of the solution was spray-dried, and to 90 L of the concentrate, the same amount of a 2% (w/v) aqueous solution of sodium hydroxide was added. The solution was stirred while maintained at 20° C. to 25° C. Subsequently, the solution was centrifuged, and 260 g of a sodium hydroxide-treated product was obtained. This sodium hydroxide-treated product was washed with water. Subsequently, centrifugation was carried out, a precipitate was freeze-dried and washed with water, and then 90.7 g of a powder was obtained. The powder was washed again with water, and then was dissolved in ethanol. The resultant was subjected to suction filtration. An ethanol-eluted component was concentrated, and 76.3 g of a high nobiletin- and tangeretin-containing powder (percentage content of nobiletin: 50.2 wt %, and percentage content of tangeretin: 31.2 wt %) was obtained. The recovery ratio was 25.2%.

Example 5

55 g of a dried pomace of Taiwan tangerine was immersed in 450 ml of 30% (v/v) ethanol, and the mixture was

TABLE 4

| | | Component | | | | |
|---|---|---|---|---|---|---|
| | | Nobiletin | | Tangeretin | | |
| Step | Total amount | Percentage content | Content | Percentage content | Content | Recovery ratio |
| Extract, after concentration (g) | 2340 g | 5.5 wt % | 128.7 g | 3.5 wt % | 81.9 g | 60.1% |
| NaOH treatment, before drying | 319 g | | 26.8 g | | 28.6 g | 15.8% |
| NaOH treatment, after drying | 92.5 g | 28.9 wt % | 26.8 g | 30.9 wt % | 28.6 g | 15.8% |
| After washing with water | — | — | — | — | — | — |
| EtOH eluate | 62.5 g | 42.8 wt % | 26.8 g | 45.9 wt % | 28.6 g | 15.8% |

[Lot 2]

55 kg of a dried pomace of Taiwan tangerine was subjected to extraction for 1 hour at 60° C. using 450 L of 30% (v/v) ethanol. The extract was left to stand overnight at room temperature, and then was filtered through a cartridge filter (retention particle size: 10 μm). Subsequently, the filtrate was concentrated, and the amount of the solution was decreased to 80 L. A 2% (w/v) aqueous solution of sodium hydroxide in the same amount as that of the solution was added thereto, and the solution was stirred while kept cold at 6° C. Subsequently, the solution was centrifuged, and 1534 g of a sodium hydroxide-treated product was obtained. 1294 g of the sodium hydroxide-treated product thus obtained was washed with water. Thereafter, centrifugation was carried out, and thus the product was separated into a supernatant and a precipitate. The precipitate was freeze-dried, and then was washed with water, and 92.6 g of a powder was obtained. The powder was washed with water again, and then was dissolved in ethanol, and suction filtration was carried out. The ethanol-eluted component was concentrated, and thus 58.2 g of a high nobiletin- and tangeretin-containing powder (percentage content of nobiletin: 54.2 wt %, and percentage content of tangeretin: 36.0 wt %) was obtained. The recovery ratio was 24.3%.

subjected to extraction for 2 hours in a water bath at 70° C. The extract was filtered through a nonwoven fabric. A portion of the extract was concentrated and weighed, and the contents of nobiletin and tangeretin were calculated by performing a HPLC analysis. The same operation was carried out using 40% (v/v), 50% (v/v) and 70% (v/v) ethanol instead of 30% (v/v) ethanol. The recovery ratio was calculated based on 275 mg, which was assumed to be contained in 55 g of the dried pomace. The results are presented in Table 5.

TABLE 5

| | | Nobiletin | | Tangeretin | | |
|---|---|---|---|---|---|---|
| | Weight | Percentage content | Content | Percentage content | Content | Recovery ratio |
| 30% | 2268 mg | 3.9 wt % | 89 mg | 1.7 wt % | 37 mg | 46.2% |
| 40% | 2525 mg | 3.2 wt % | 81 mg | 1.5 wt % | 38 mg | 43.1% |
| 50% | 1770 mg | 4.0 wt % | 71 mg | 2.2 wt % | 39 mg | 39.9% |
| 70% | 1831 mg | 3.9 wt % | 71 mg | 2.1 wt % | 38 mg | 39.9% |

Example 6

55 kg of a dried pomace of Taiwan tangerine was subjected to extraction for 6 hours at 60° C. using 450 L of 30%

(v/v) ethanol. The extract was left to stand overnight at room temperature, and then was filtered through a cartridge filter (retention particle size: 10 μm). Subsequently, the filtrate was concentrated, the amount of the solution was decreased to 130 L, and this was used as a Taiwan tangerine extract. To 5 g of a freeze-dried powder of this Taiwan tangerine extract (containing 195 mg (3.9% by weight) of nobiletin and 100 mg (2.0% by weight) of tangeretin), 30 ml of a 1% (w/v) aqueous solution of sodium hydroxide was added, and a Taiwan tangerine alkali-treated product was obtained. This alkali-treated product was stirred by rotation for 16 hours, and then was centrifuged. Thus, precipitate 1 was obtained. This precipitate 1 was washed with water and then centrifuged, and precipitate 2 was obtained. This process was performed until the supernatant became neutral. 100% (v/v) Ethanol was added to a product (1.1 g) obtained by drying the precipitate finally obtained, and the mixture was centrifuged. A filtrate thus obtained was concentrated, and thus 344 mg of a powder was obtained. This powder contained 159 mg (46.3% by weight) of nobiletin and 87 mg (25.3% by weight) of tangeretin. According to the present method, 80% or more of nobiletin and tangeretin contained in the freeze-dried powder could be recovered.

Example 7

55 kg of a dried pomace of Taiwan tangerine was subjected to extraction for 6 hours at 60° C. using 450 L of 30% (v/v) ethanol. The extract was left to stand overnight at room temperature, and then was filtered through a cartridge filter (retention particle size: 10 μm). Subsequently, the filtrate was concentrated, the amount of the solution was decreased to 130 L, and this was used as a Taiwan tangerine extract. To 4.5 g of a concentrated and solid-dried product of this Taiwan tangerine extract (containing 175 mg (3.9% by weight) of nobiletin and 90 mg (2.0% by weight) of tangeretin), 30 ml of a 1 w/v % aqueous solution of sodium hydroxide was added, and a Taiwan tangerine alkali-treated product was obtained. This alkali-treated product was stirred by rotation for 16 hours, and then was centrifuged. Thus, precipitate 1 was obtained. This precipitate 1 was washed with water and then centrifuged, and precipitate 2 was obtained. This process was performed until the supernatant became neutral. 100% (v/v) Ethanol was added to a product (760 mg) obtained by drying the precipitate finally obtained, and the mixture was centrifuged. A filtrate thus obtained was concentrated, and thus 344 mg of a powder was obtained. The filtrate contained 159 mg (44.2% by weight) of nobiletin and 87 mg (22.7% by weight) of tangeretin. According to the present method, 60% or more of nobiletin and tangeretin contained in the concentrate could be recovered.

Reference Example 1

589 g (wet weight) of the leaves of Taiwan tangerine were weighed, and the leaves were dried for 16 hours at about 80° C. using a drying machine (TOKYO RIKAKIKAI CO., LTD., WFO-1001 SD). Thus, 218 g of dried leaves were obtained. To 5 g of the dried leaves thus obtained, 100 mL of distilled water at about 70° C. was added thereto, the mixture was placed in a water bath at about 70° C., and heating and extraction was carried out for 3 hours. The extract thus obtained was subjected to suction filtration using a Buchner filter provided with a filter paper (manufactured by Advantec MFS, Inc., No. 131) having a retention particle size of 3 μm spread thereon, and thus a residue was obtained.

The residue thus obtained was dried, and 30% (v/v) ethanol in an amount of 2 times the weight of the residue was added thereto. Ethanol extraction was carried out for 3 days at room temperature. The extract was subjected to suction filtration using a Buchner funnel provided with a filter paper (manufactured by Advantec MFS, Inc., No. 131) having a retention particle size of 3 μm spread thereon, and a filtrate was obtained. The filtrate thus obtained was concentrated with a rotary evaporator, and a concentrate in a solid-dry state was obtained. Water and ethyl acetate in amounts equal to the weight of the concentrate thus obtained were added to the concentrate to thereby dissolve the concentrate, and partition was carried out. The ethyl acetate-soluble component was concentrated, and an extract having a nobiletin percentage content of 24.4 wt % and a tangeretin percentage content of 11.2 wt % was obtained.

Reference Example 2

100 mL of distilled water at about 70° C. was added to 5 g of dried leaves of Taiwan tangerine, the mixture was placed in a water bath at about 70° C., and heating and extraction was carried out for 3 hours. The extract thus obtained was subjected to suction filtration using a Buchner funnel provided with a filter paper (manufactured by Advantec MFS, Inc., No. 131) having a retention particle size of 3 μm spread thereon, and a residue was obtained.

The residue thus obtained was dried, and 100% (v/v) ethanol in an amount of 2 times the weight of the residue was added thereto. Ethanol extraction was carried out for 3 days at room temperature. The extract was subjected to suction filtration using a Buchner funnel provided with a filter paper (manufactured by Advantec MFS, Inc., No. 131) having a retention particle size of 3 μm spread thereon, and a filtrate was obtained. The filtrate thus obtained was concentrated with a rotary evaporator, and a concentrate in a solid-dry state was obtained. Water and ethyl acetate in amounts equal to the weight of the concentrate thus obtained were added to the concentrate to thereby dissolve the concentrate, and partition extraction was carried out. The ethyl acetate-soluble component was concentrated, and an extract having a nobiletin percentage content of 6.9 wt % and a tangeretin percentage content of 5.2 wt % was obtained.

Reference Example 3

100 mL of distilled water at about 70° C. was added to 5 g of dried leaves of Taiwan tangerine, the mixture was placed in a water bath at about 70° C., and heating and extraction was carried out for 3 hours. The extract thus obtained was subjected to suction filtration using a Buchner funnel provided with a filter paper (manufactured by Advantec MFS, Inc., No. 131) having a retention particle size of 3 μm spread thereon, and a residue was obtained.

The residue thus obtained was dried, and 100% (v/v) ethanol in an amount of 2 times the weight of the residue was added thereto. Ethanol extraction was carried out for 3 days at room temperature. The extract was subjected to suction filtration using a Buchner funnel provided with a filter paper (manufactured by Advantec MFS, Inc., No. 131) having a retention particle size of 3 μm spread thereon, and a filtrate was obtained. The filtrate thus obtained was concentrated with a rotary evaporator, and a concentrate in a solid-dry state was obtained. Water and ethyl acetate in amounts equal to the weight of the concentrate thus obtained were added to the concentrate to thereby dissolve the concentrate, and partition was carried out. The ethyl acetate-soluble component was concentrated, and an extract having a nobiletin percentage content of 6.9 wt % and a tangeretin percentage content of 5.2 wt % was obtained. In the same manner, extraction was carried out using 30% (v/v) ethanol, 50% (v/v) ethanol, and 70% (v/v) ethanol, respectively, instead of 100% (v/v) ethanol. The results are presented in Table 6.

TABLE 6

| Ethanol concentration (%) | Weight of ethyl acetate extract (mg) | Percentage content (%) | |
|---|---|---|---|
| | | Nobiletin | Tangeretin |
| 30 | 82 | 24.4 | 11.2 |
| 50 | 122 | 18.0 | 15.5 |
| 70 | 174 | 13.2 | 7.9 |
| 100 | 361 | 6.9 | 5.2 |

From the above results, it is understood that when the ethanol concentration increases, the weight of the ethyl acetate extract is increased; however, the contents of nobiletin and tangeretin are larger when 30% (v/v) ethanol or 50% (v/v) ethanol is used, and the extraction efficiency is high when ethanol at these concentrations is used. As described above, fractions containing nobiletin and tangeretin at high concentrations were obtained even from the leaves of Taiwan tangerine. Since the fractions thus obtained contain nobiletin and tangeretin at concentrations several times higher compared with the fractions that have been produced hitherto, these compounds can be conveniently produced. Furthermore, when the high concentration fractions obtained by the method of the present invention are used, superiority is increased in view of cost on the occasion of producing these compounds and analogues thereof.

INDUSTRIAL APPLICABILITY

The present invention is useful in the fields of food, pharmaceutical products and cosmetic products, and is particularly useful as a cream preparation, a gel cream preparation and a skin lotion, or from the viewpoint of being incorporable into these products.

The invention claimed is:
1. A method of manufacturing a composition containing nobiletin and tangeretin, comprising the following Steps (2), (3) and (4):
   (2) a step of treating fruit, fruit peel, or pomace of citrus fruit with 20 to 70% (v/v) ethanol that is maintained at a temperature of 50° C. to 70° C. to obtain a nobiletin and tangeretin solution, wherein the nobiletin and tangeretin solution is obtained as a liquid component by filtration with a filter having a retention particle size of 3 μm to 10 μm;
   (3) a step of concentrating and/or drying the nobiletin and tangeretin solution to obtain a nobiletin and tangeretin concentrate; and
   (4) a step of treating the nobiletin and tangeretin concentrate with a 0.1% to 20% (w/v) aqueous alkaline solution to obtain a composition containing nobiletin and tangeretin as an insoluble component.
2. The method according to claim 1, wherein the Step (2) is a step of treating citrus fruit for 1 to 8 hours.
3. The method according to claim 1, wherein the solvent is 20 to 50% (v/v) ethanol.
4. The method according to claim 1, wherein the Step (4) is a step of treating the nobiletin and tangeretin concentrate with a 1 to 3% (w/v) aqueous alkaline solution at room temperature to obtain a composition containing nobiletin and tangeretin as an insoluble component.
5. The method according to claim 1, wherein the citrus fruit is at least one plant selected from the group consisting of *Citrus depressa, C. unshiu, C. tachibana, C. leiocarpa, C. tardiva, C. succosa, C. kinokuni, C. erythrosa, C. sunki, C. deliciosa, C. nobilis, C. retuculata, C. tangerina, C. hanayu, C. reticulata, C. sunki, C. nippokoreana*, shiranuhi, and kiyomi.
6. The method according to claim 1, wherein the step (4) is a step of treating the nobiletin and tangeretin concentrate with a 0.1% to 20% (w/v) aqueous alkaline solution at a temperature of 6° C. to room temperature to obtain a composition containing nobiletin and tangeretin as an insoluble component.
7. The method according to claim 1, wherein the steps (3) and (4) are continuously executed.

* * * * *